United States Patent
Lin

(10) Patent No.: US 10,722,676 B2
(45) Date of Patent: Jul. 28, 2020

(54) GAS GENERATOR

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 185 days.

(21) Appl. No.: 15/912,819

(22) Filed: Mar. 6, 2018

(65) Prior Publication Data

US 2018/0250489 A1    Sep. 6, 2018

(30) Foreign Application Priority Data

Mar. 6, 2017  (CN) .......................... 2017 1 0127527

(51) Int. Cl.
| | | |
|---|---|---|
| *A61M 16/12* | (2006.01) | |
| *C25B 1/04* | (2006.01) | |
| *A61M 16/20* | (2006.01) | |
| *A61M 16/10* | (2006.01) | |
| *A61M 16/14* | (2006.01) | |
| *A61M 15/08* | (2006.01) | |
| *C25B 15/02* | (2006.01) | |

(52) U.S. Cl.
CPC .......... *A61M 16/12* (2013.01); *A61M 16/201* (2014.02); *C25B 1/04* (2013.01); *C25B 15/02* (2013.01); *A61M 15/08* (2013.01); *A61M 16/107* (2014.02); *A61M 16/14* (2013.01); *A61M 2205/0233* (2013.01); *A61M 2205/3331* (2013.01); *A61M 2205/3382* (2013.01); *Y02E 60/366* (2013.01)

(58) Field of Classification Search
None
See application file for complete search history.

(56) References Cited

U.S. PATENT DOCUMENTS

| | | | | |
|---|---|---|---|---|
| 10,465,300 B2* | 11/2019 | Lin | ....................... | C02F 1/4618 |
| 2004/0065542 A1* | 4/2004 | Fairfull | ..................... | C25B 9/06 |
| | | | | 204/228.2 |
| 2007/0210063 A1* | 9/2007 | Conrad | ................. | A47J 37/067 |
| | | | | 219/449.1 |
| 2007/0217995 A1* | 9/2007 | Matsumura | ............... | C25B 1/04 |
| | | | | 423/657 |
| 2010/0236921 A1* | 9/2010 | Yang | ........................ | C25B 1/04 |
| | | | | 204/264 |
| 2014/0374243 A1* | 12/2014 | Lin | ........................... | C25B 9/00 |
| | | | | 204/228.3 |

(Continued)

FOREIGN PATENT DOCUMENTS

| | | |
|---|---|---|
| CN | 1661134 A | 8/2015 |
| CN | 106435633 A | 2/2017 |

(Continued)

*Primary Examiner* — Harry D Wilkins, III

(57) ABSTRACT

The present invention provides a gas generator including an electrolytic device, a gas pathway, and a three-way valve module. The electrolytic device is configured for electrolyzing electrolyzed water to generate gas with hydrogen. The gas generated from the electrolytic device is transferred by the gas pathway for inhaling. The three-way valve module is configured on the electrolytic device for balancing a pressure in the electrolytic device by importing an ambient gas. The present invention uses the three-way valve module to balance the pressure in the electrolytic device for maintaining the water level of the electrolyzed water, thereby avoiding the electrolyzed water splashing or corroding the other elements.

20 Claims, 8 Drawing Sheets

(56) References Cited

U.S. PATENT DOCUMENTS

| | | | |
|---|---|---|---|
| 2014/0374246 A1 | 12/2014 | Lin | |
| 2015/0101601 A1* | 4/2015 | Lin | C25B 1/04 128/202.26 |
| 2016/0108528 A1* | 4/2016 | Lin | C02F 1/4618 204/276 |
| 2019/0218676 A1* | 7/2019 | Noda | C25B 1/08 |

FOREIGN PATENT DOCUMENTS

| | | |
|---|---|---|
| KR | 101244629 | 3/2013 |
| TW | 201326535 | 7/2013 |
| TW | M518089 | 3/2016 |
| TW | 201706002 | 2/2017 |

* cited by examiner

GAS GENERATOR

CROSS-REFERENCE TO RELATED APPLICATIONS

This application claims the priority benefit of Chinese Application Serial No. 201710127527.4 filed Mar. 6, 2017 the disclosure of which is incorporated herein by reference.

BACKGROUND OF THE INVENTION

1. Field of the Invention

The present invention relates to a gas generator, and more particularly, to a gas generator balancing the pressure in the electrolytic device.

2. Description of the Prior Art

As people have always been paying much attention on health developments, many developments in medical technology are often targeted on treating diseases and prolonging human life. Most of the treatments in the past are passive, which means that the disease is treated only when it occurs. The treatments include an operation, a medication treatment, a radiation therapy, or even a medical treatment for cancer. However, in recent years, most of the researches from medical experts are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and have become increasingly popular to the general public.

Studies have found that there are instable oxygen species (O+), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but the lung damage could be ameliorated by inhaling hydrogen.

The hydrogen for inhaling is usually generated from electrolyzing water by an electrolytic device. The temperature of the electrolytic device rises up while the electrolytic device is working. However, the electrolytic device is cooling down after shutdown and then negative pressure is generated. Due to the negative pressure inside the electrolytic device, the external moisture or liquid water is flowing into the electrolytic device. Therefore, the liquid surface within the electrolytic device may be unstable, thereby causing the security risk of using electrolytic device.

SUMMARY OF THE INVENTION

The present invention is directed to providing a gas generator for electrolyzing water to generate gas with hydrogen and mixing the gas with hydrogen with atomized gas to generate a healthy gas for human to inhale. At the same time, the three-way valve module is used to balance the pressure in the electrolytic device for maintaining the water level of the electrolyzed water, thereby avoiding the electrolyzed water splashing or corroding the other elements.

The gas generator of the present invention comprises an electrolytic device, a gas pathway, a replenishing cup, and a three-way valve module. The electrolytic device accommodates the electrolyzed water comprising an electrolyte. The electrolytic device is configured for electrolyzing the electrolyzed water to generate the gas with hydrogen. The gas pathway is coupled to the electrolytic device, for transferring the gas with hydrogen. The replenishing cup is configured for accommodating the replenished water to supplement the replenished water to the electrolytic device. The three-way valve module comprises a first conduit and a switch, wherein a first end of the first conduit is coupled to the electrolytic device and a second end of the first conduit is connected to the exterior of the gas generator, and the switch selectively couples the first end to the second end.

Wherein when the electrolytic device stops electrolyzing the electrolyzed water and the replenishing cup stops supplementing the replenished water to the electrolytic device, the switch couples the first end to the second end, and so that the electrolytic device is connected to the exterior of the gas generator via the first conduit.

In an embodiment, when the electrolytic device stops electrolyzing the electrolyzed water and the replenishing cup supplements the replenished water to the electrolytic device; the switch blocks the conduction between the first end and the second end.

In an embodiment, the three-way valve module comprises a one-way valve configured in the first conduit, and the one-way valve only allows the external gas of the gas generator to flow into the electrolytic device unidirectionally.

In an embodiment, the gas generator further comprises a pump coupled to the electrolytic device when the electrolytic device stops electrolyzing the electrolyzed water and the replenishing cup supplements the replenished water to the electrolytic device, the pump generates negative pressure within the electrolytic device.

In an embodiment, the three-way valve further comprises a second conduit. A third end of the second conduit is coupled to the switch, and a fourth end of the second conduit is coupled to the electrolytic device or connected to the exterior of the gas generator. The pump is configured in the second conduit. When the electrolytic device stops electrolyzing the electrolyzed water and the replenishing cup supplements the replenished water to the electrolytic device, the switch couples the first conduit to the second conduit, so that the electrolytic device is connected to the exterior of the gas generator.

In an embodiment, when the electrolytic device stops electrolyzing the electrolyzed water and the replenishing cup stops supplementing the replenished water to the electrolytic device, the switch blocks the connection between the first conduit and the second conduit.

In an embodiment, when the electrolytic device electrolyzes the electrolyzed water, the switch blocks the connection between the first conduit and the second conduit.

In an embodiment, the switch can be a solenoid valve when the solenoid valve is activated, and the solenoid valve can block the conduction between the first end and the second end.

In an embodiment, the gas generator further comprises an atomizing device coupled to the gas pathway for generating
} atomized gas and receiving the gas with hydrogen to mix the atomized gas with the gas with hydrogen to generate a healthy gas.

In an embodiment, the replenishing cup is coupled to the gas pathway.

Another object of the present invention is to provide a gas generator comprising an electrolytic device, a gas pathway, a replenishing cup, and a three-way valve module. The electrolytic device is configured for accommodating the electrolyzed water comprising an electrolyte. The electrolytic device is configured for electrolyzing the electrolyzed water to generate the gas with hydrogen. The gas pathway is coupled to the electrolytic device for transferring the gas with hydrogen. The replenishing cup is configured for accommodating the replenished water to supplement the replenished water to the electrolytic device. The three-way valve module configured between the electrolytic device and the exterior of the gas generator, wherein the three-way valve module comprises a first conduit, a second conduit, and a switch disposed between the first conduit and the second conduit. When the electrolytic device electrolyzes the electrolyzed water, the switch blocks the connection between the first conduit and the second conduit.

Besides, the three-way valve module comprises a one-way valve configured in the first conduit, and the one-way valve only allows the external gas of the gas generator to flow into the electrolytic device unidirectionally.

In an embodiment, a first end of the first conduit is coupled to the electrolytic device and a second end of the first conduit is connected to the exterior of the gas generator. When the electrolytic device stops electrolyzing the electrolyzed water and the replenishing cup supplements the replenished water to the electrolytic device, the switch blocks the conduction between the first end and the second end.

In an embodiment, the gas generator further comprises a pump coupled to the electrolytic device. When the electrolytic device stops electrolyzing the electrolyzed water and the replenishing cup supplements the replenished water to the electrolytic device, the pump generates negative pressure in the electrolytic device.

In an embodiment, when the electrolytic device stops electrolyzing the electrolyzed water and the replenishing cup supplements the replenished water to the electrolytic device, the switch couples the first conduit to the second conduit, such that the electrolytic device is connected to the exterior of the gas generator via the second conduit.

In an embodiment, when the electrolytic device stops electrolyzing the electrolyzed water and the replenishing cup stops supplementing the replenished water to the electrolytic device, the switch makes the electrolytic device connected to the exterior of the gas generator via the first conduit.

In an embodiment, when the electrolytic device stops electrolyzing the electrolyzed water and the replenishing cup stops supplementing the replenished water to the electrolytic device, the switch blocks the conduction between the first conduit and the second conduit.

In an embodiment, the switch can be a solenoid valve. When the solenoid valve is activated, the solenoid valve can block the conduction of the first conduit.

In an embodiment, the gas generator further comprises an atomizing device coupled to the gas pathway for generating atomized gas and receiving the gas with hydrogen to mix the atomized gas with the gas with hydrogen to generate a healthy gas.

In an embodiment, the replenishing cup is coupled to the gas pathway.

To summarize, the objective of the present invention is to provide a gas generator comprising an electrolytic device, a gas pathway, a replenishing cup, and a three-way valve module. The gas with hydrogen generated by the electrolytic device in the gas generator of the present invention is for inhaling. The three-way valve module is provided in the electrolytic device, in order to adjust the pressure inside the electrolytic device, so that the liquid level of the electrolyzed water does not become unpredictable due to the pressure difference, thereby avoiding the electrolyzed water splashing or corroding the other elements.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
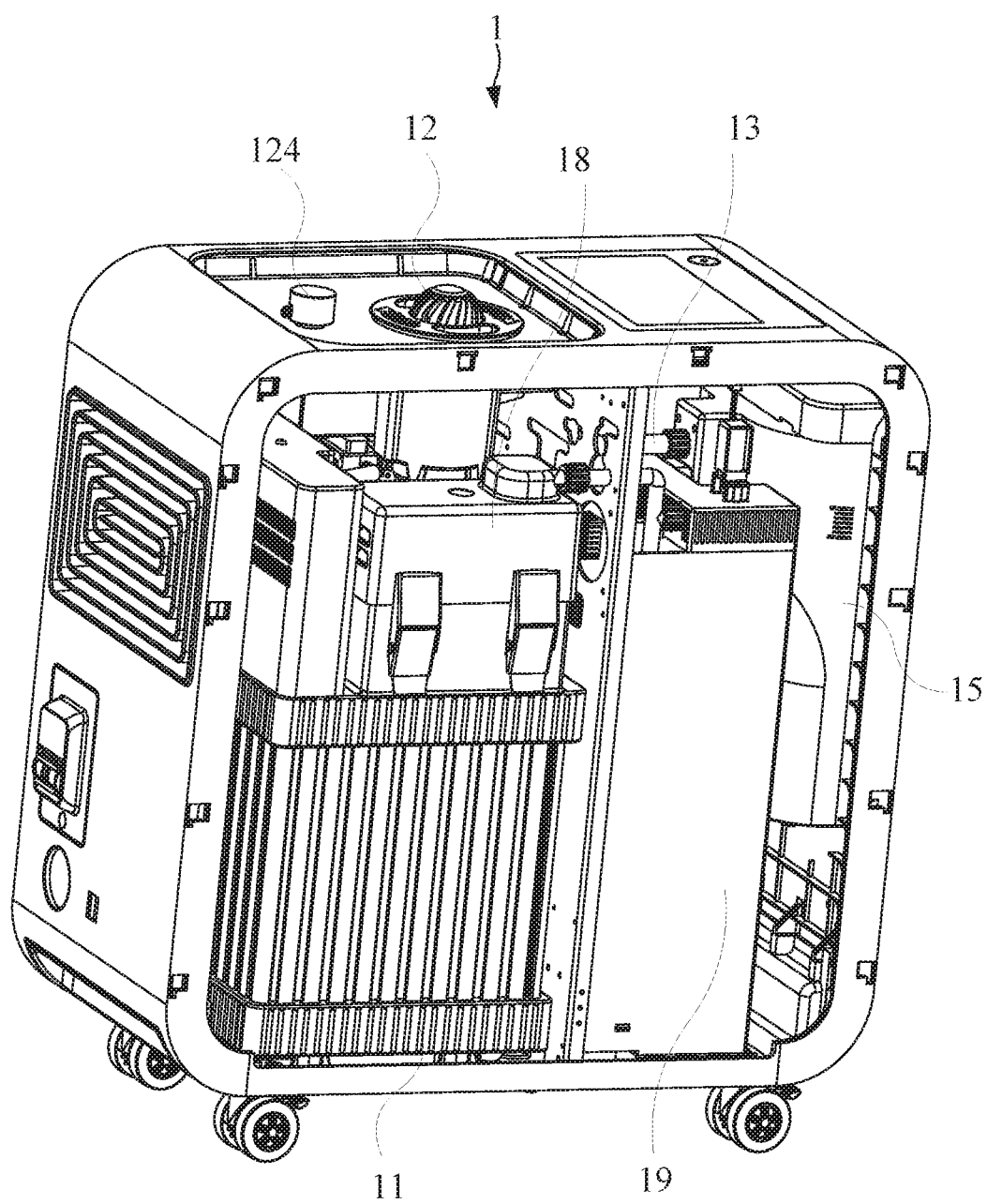
FIG. 1 and FIG. 2 show a schematic diagram of the gas generator in an embodiment with different visual angles of the present invention.
Figure 2:
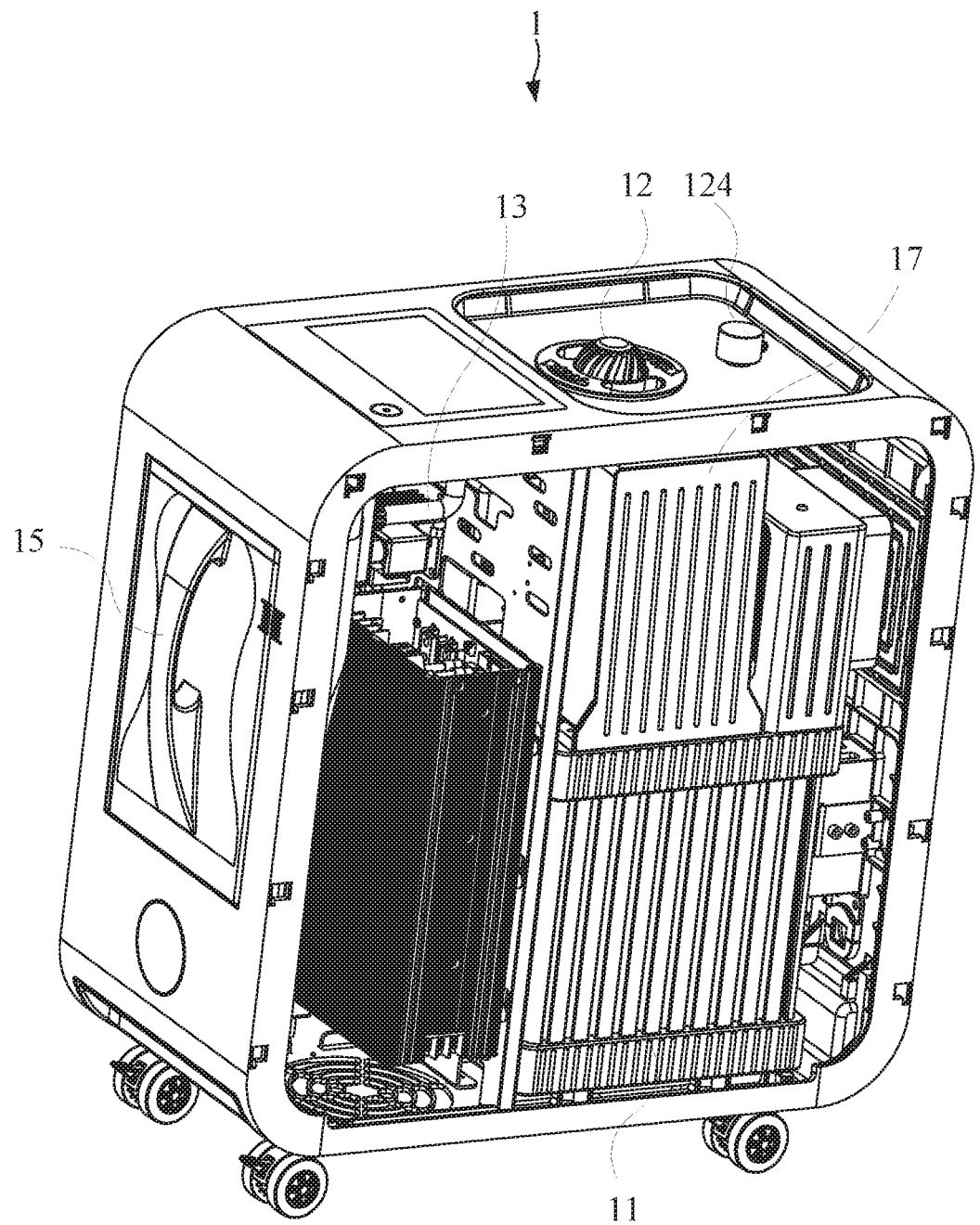
Figure 3:
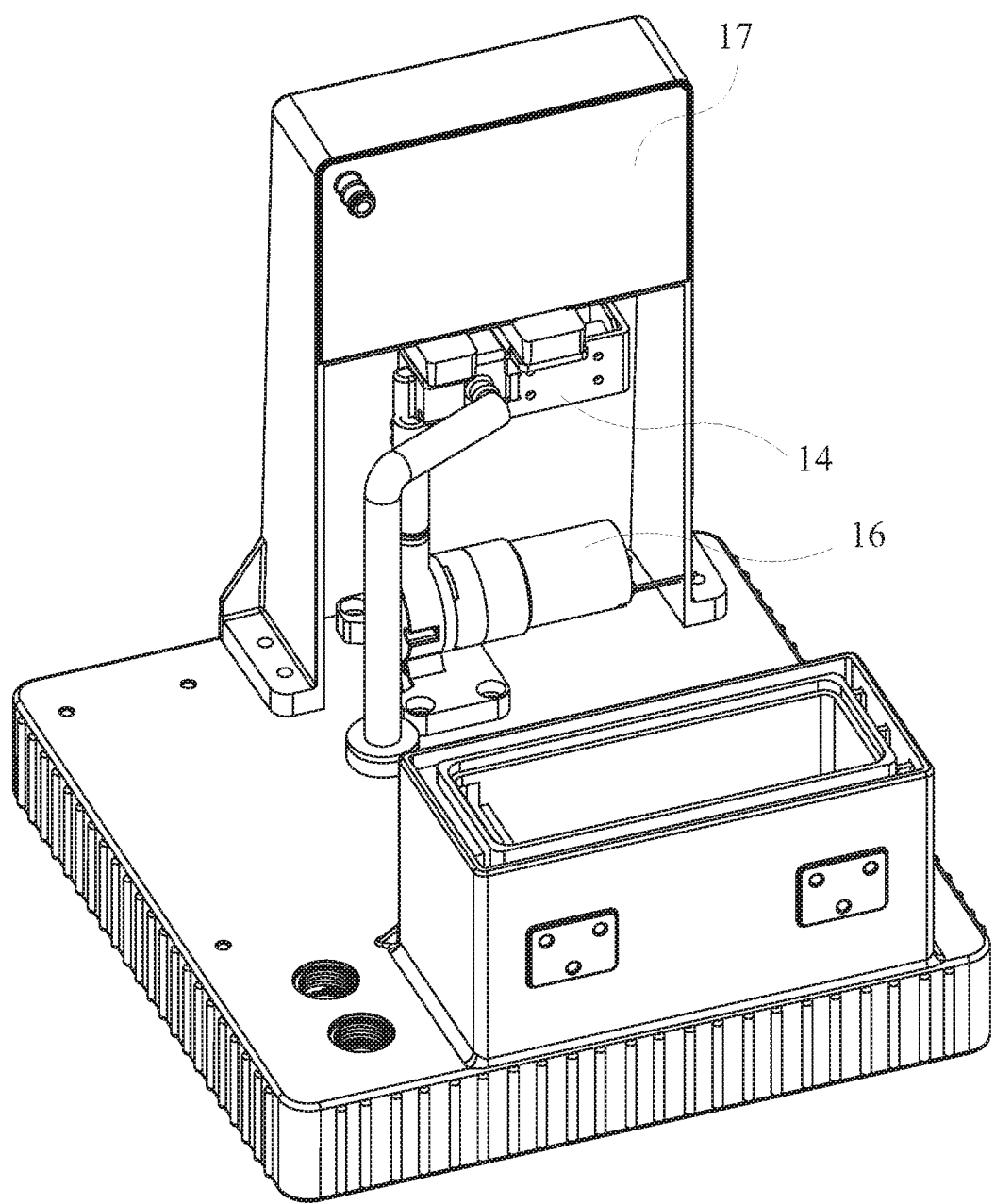
FIG. 3 and FIG. 4 show a schematic diagram of the three-way valve module in the gas generator in an embodiment with different visual angles of the present invention.
Figure 4:
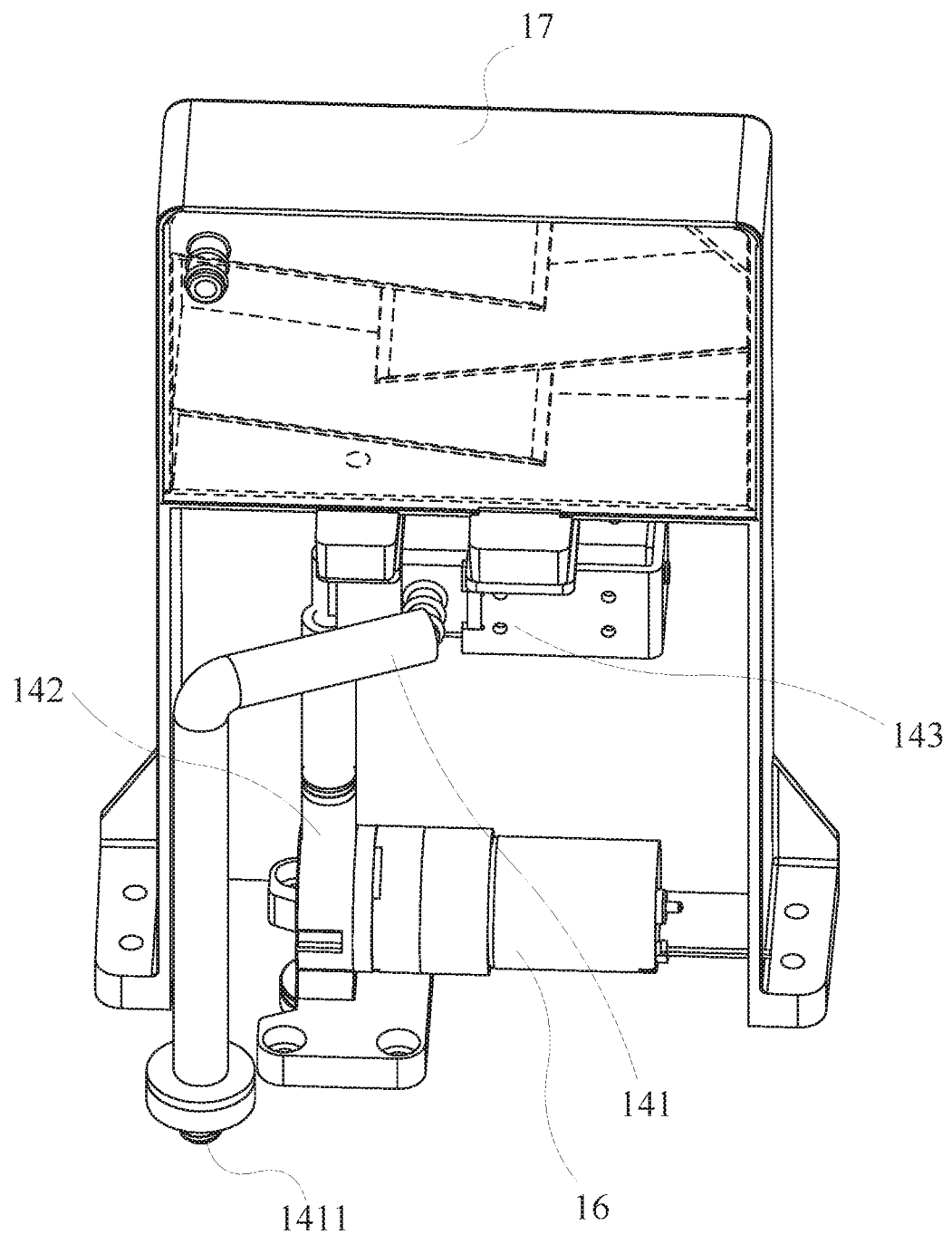

Please refer to FIG. 1, FIG. 2, FIG. 3, and FIG. 4. FIG. 1 and FIG. 2 show a schematic diagram of the gas generator 1 in an embodiment with different visual angles of the present invention. FIG. 3 and FIG. 4 show a schematic diagram of the three-way valve 14 module in the gas generator 1 in an embodiment with different visual angles of the present invention. The gas generator 1 of the present invention comprises the electrolytic device 11, a gas pathway 13, a replenishing cup 15, and a three-way valve module 14. The electrolytic device 11 accommodates the electrolyzed water comprising an electrolyte; the electrolytic device 11 is configured for electrolyzing the electrolyzed water to generate gas with hydrogen. The gas pathway 13 is coupled to the electrolytic device 11 for transferring the gas with hydrogen. The replenishing cup 15 is configured for accommodating the replenished water to supplement the replenished water to the electrolytic device 11. The three-way valve module 14 comprises a first conduit 141 and a switch 143, wherein a first end 1412 of the first conduit 14 is coupled to the electrolytic device 11 and a second end 1413 of the first conduit 14 is connected to the exterior of the gas generator 1, and the switch 143 selectively couples the first end 1412 to the second end 1413.

Wherein when the electrolytic device 11 stops electrolyzing the electrolyzed water and the replenishing cup 15 stops supplementing the replenished water to the electrolytic device 11, the switch 143 couples the first end 1412 to the second end 1413 of the first conduit 141, and the electrolytic device 11 is connected to the exterior of the gas generator 1 via the first conduit 141. Therefore, the pressure in the electrolytic device 11 is kept in balance with the pressure outside the gas generator 1.

When the electrolytic device 11 stops electrolyzing the electrolyzed water and the replenishing cup 15 supplements the replenished water to the electrolytic device 11, the switch 143 blocks the conduction between the first end 1412 and the second end 1413.

In an embodiment, the three-way valve module 14 comprises a one-way valve 1411 configured in the first conduit 141, and the one-way valve 141 only allows the external gas of the gas generator 1 to flow into the electrolytic device 11 unidirectionally. Thereby the gas (e.g., gas with hydrogen) and the liquid (e.g., electrolyte) in the electrolytic device 11 do not escape through the first conduit 141 to the exterior of the gas generator 1, and the gas generator 1 is safe to use.

In an embodiment, the gas generator 1 further comprises a pump 16 coupled to the electrolytic device 11. When the electrolytic device 11 stops electrolyzing the electrolyzed water and the replenishing cup 15 supplements the replenished water to the electrolytic device 11, the pump 16 generates negative pressure within the electrolytic device 11 to supplement the replenished water. Wherein, the negative pressure as described can be a pressure less than the pressure of the external environment, and the pump 16 makes negative pressure in the electrolytic device 11 in a way that the gas in the electrolytic device 11 is evacuated and exhausted out of the electrolytic device 11. The gas generator 1 can supplement the replenished water into the electrolytic device 11 by a pressure difference.

In practice, the electrolytic device 11 may comprise a water level gauge (not shown) for detecting the height of the electrolyzed water in the electrolytic device 11 and thereby limiting the amount of water replenished back to the electrolytic device 11.

The gas generator 1 further comprises an atomizing device 12 coupled to the gas pathway 13 for generating atomized gas and receiving the gas with hydrogen to mix the atomized gas with the gas with hydrogen to generate a healthy gas for inhaling.

Figure 7:
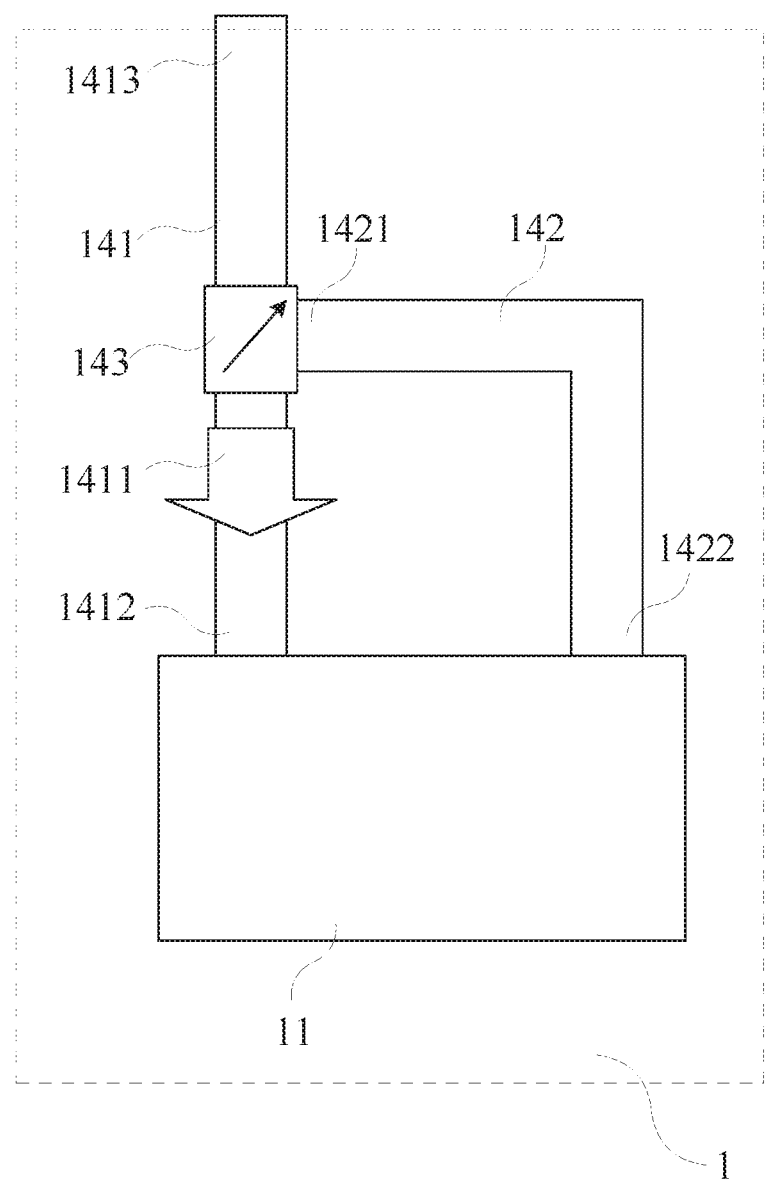
FIG. 7 illustrates a schematic diagram of the three-way valve module of the gas generator in an embodiment of the present invention.

Please refer to FIG. 4 and FIG. 7. FIG. 7 illustrates a schematic diagram of the three-way valve module 14 of the gas generator 1 in an embodiment of the present invention. The three-way valve 14 further comprises a second conduit 142; a third end 1421 of the second conduit is coupled to the switch 143; and a fourth end 1422 of the second conduit 142 is coupled to the electrolytic device 11 or connected to the exterior of the gas generator 1. When the pump 16 generates negative pressure in the electrolytic device 11 to allow the electrolytic device 11 to supplement the replenished water by a pressure difference, the switch 143 can make the fourth end 1422 of the second conduit 142 couple to the second end 1413 of the first conduit 141, so that the electrolytic device 11 is connected to the exterior of the gas generator 1, and exhausts the excess gas caused by the reduction of the gas volume of the electrolytic device 11 due to the replenishment. Wherein, the pump 16 is provided in the second conduit 142 and the one-way valve 1411 may be provided at the first end 1412 of the first conduit 141.

Figure 8:
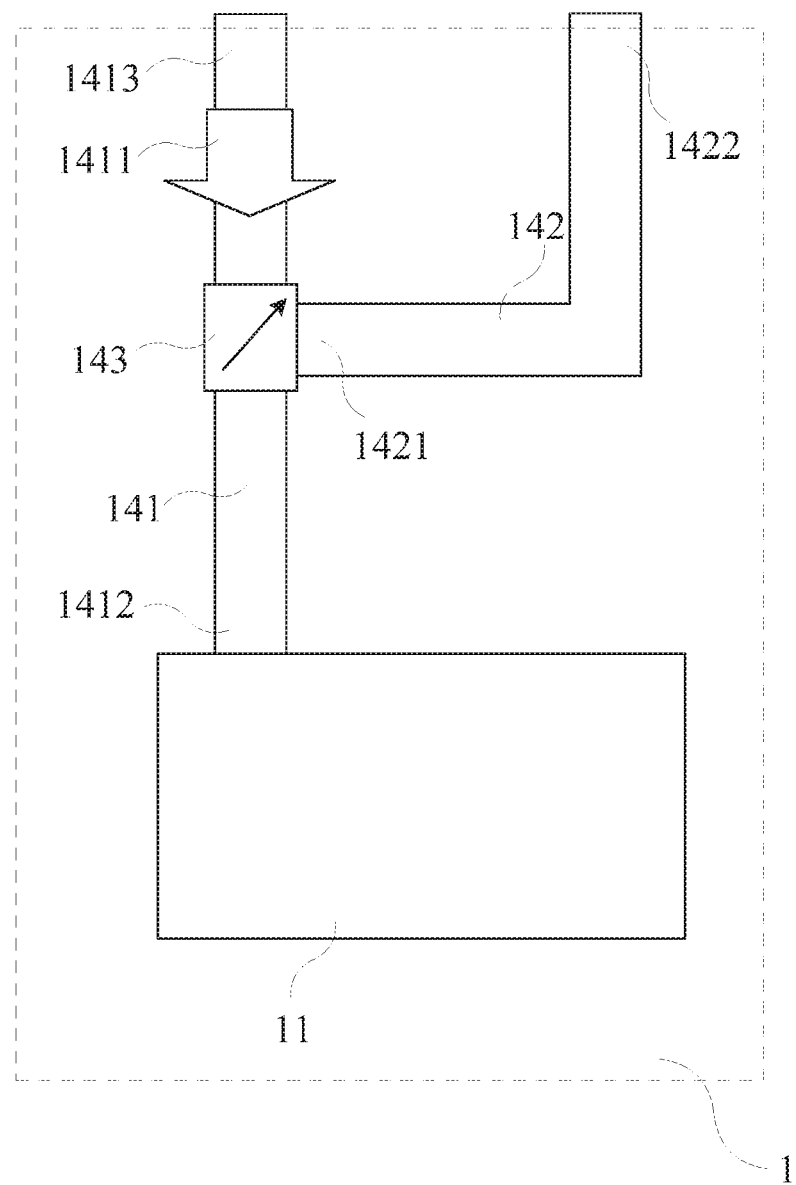
FIG. 8 illustrates a schematic diagram of the three-way valve module of the gas generator in another embodiment of the present invention.

Please refer to FIG. 8. FIG. 8 illustrates a schematic diagram of the three-way valve module 14 of the gas generator 1 in another embodiment of the present invention. In another embodiment, the fourth end 1422 of the second conduit 142 is connected to the exterior of the gas generator 1. When the pump 16 generates negative pressure in the electrolytic device 11 to allow the electrolytic device 11 to supplement the water by the pressure difference, the switch 143 can make the fourth end 1422 of the second conduit 142 couple to the first end 1412 of the first conduit 141, so that the electrolytic device 11 is connected to the exterior of the gas generator 1.

Please refer to FIG. 1, FIG. 2, FIG. 7, and FIG. 8. Another category of the present invention is a gas generator 1 comprises the electrolytic device 11, a gas pathway 13, a replenishing cup 15, and a three-way valve module 14. The electrolytic device 11 accommodates the electrolyzed water of the electrolyte. The electrolytic device 11 is configured for electrolyzing the electrolyzed water to generate the gas with hydrogen. The gas pathway 13 is coupled to the electrolytic device 11, for transferring the gas with hydrogen. The replenishing cup 15 is configured for accommodating the replenished water to supplement the replenished water to the electrolytic device 11. The three-way valve module 14 is configured between the electrolytic device 11 and the exterior of the gas generator 1, wherein the three-way valve module 14 comprises a first conduit 141, a second conduit 142, and a switch 143 disposed between the first conduit 141 and the second conduit 142. When the electrolytic device 11 electrolyzes the electrolyzed water, the switch 143 blocks the connection between the first conduit 141 and the second conduit 142.

Wherein the three-way valve module 14 comprises a one-way valve 1411 configured in the first conduit 141, and the one-way valve 141 only allows the external gas of the gas generator 1 to flow into the electrolytic device 11 unidirectionally.

When the electrolytic device 11 stops electrolyzing the electrolyzed water and the replenishing cup 15 supplements the replenished water to the electrolytic device 11, the switch 143 couples the first conduit 141 to the second conduit 142, and the electrolytic device 11 is connected to the exterior of the gas generator 1 via the second conduit 142.

The gas generator 1 further comprises a pump 16 coupled to the electrolytic device 11. When the electrolytic device 11 stops electrolyzing the electrolyzed water and the replenishing cup 15 supplements the replenished water to the electrolytic device 11, the pump 16 generates negative pressure in the electrolytic device 11 to supplement the replenished water.

In an embodiment, when the electrolytic device 11 stops electrolyzing the electrolyzed water and the replenishing cup 15 stops supplementing the replenished water to the electrolytic device 11, the switch 143 blocks the connection between the first conduit 141 and the second conduit 142. When the electrolytic device 11 stops supplementing the replenished water, the switch 143 blocks the connection between the first end 1412 of the first conduit 141 and the second conduit 142 and the second end 1413 of the first conduit 141 and the second conduit 142. At this time, the electrolytic device 11 is not connected to the exterior of the gas generator 1 through the second conduit 142 but can be connected to the exterior of the gas generator 1 through the one-way valve 1411, so that the pressure within the electrolytic device 11 can be balanced with the external environment.

The switch 143 can be a solenoid valve. When the solenoid valve is activated, the solenoid valve can block the conduction between the first end 1412 and the second end 1413 of the first conduit 141.

In practice, when the electrolytic device 11 electrolyzes the electrolyzed water to generate the gas with hydrogen, the gas generator 1 can shut down the solenoid valve to couple the first end 1412 to the second end 1413 of the first conduit 141 in the three-way valve module 14, and then block the connection between the first conduit 141 and the second conduit 142. When the electrolytic device 11 electrolyzes the electrolyzed water to generate the gas with hydrogen, the pressure in the electrolytic device 11 becomes greater than 1 atm. Thus, the gas with hydrogen in the electrolytic device 11 is intended to escape outwardly. However, the one-way valve 1411 provided in the first conduit 141 restricts the flow of the gas in the first conduit 141, resulting in the gas with hydrogen cannot escape via the first conduit 141, so that the gas with hydrogen can only pass through the gas pathway 13 to the atomizing device 12 to be mixed with the atomized gas to generate a healthy gas for inhaling, wherein the replenishing cup 15 is coupled to the gas pathway 13.

Please refer to FIG. 1 and FIG. 2 again. The gas generator 1 further comprises a condensation filter 18 and a wetting cup 19. The condensation filter 18 is coupled to the electrolytic device 11 for receiving and condensing the gas with hydrogen. The wetting cup 19 is coupled to the condensation filter 18, for receiving and wetting the gas with hydrogen. The gas pathway 13 is orderly coupled to the electrolytic device 11, the condensation filter 18, the wetting cup 19, the replenishing cup 15, and the atomizing device 12 to transfer the gas with hydrogen.

In practice, the water of the replenishing cup 15 can be used to supplement the wetting liquid of the wetting cup 19, or the water in the replenishing cup 15 can be drawn through the pump 16 to the electrolytic device 11 for being electrolyzed into the gas with hydrogen. At the same time, the water in the replenishing cup 15 flows in order through the wetting cup 19, the condensing filter 18 and the electrolytic device 11. The gas pathway 13 between the electrolytic device 11 and the replenishing cup 15 can be washed with water reversely. Moreover, the volatile electrolyte can be rinsed back to the electrolytic water in the electrolytic device 11, so that the electrolyte can be re-used and the consumption of electrolytes is reduced. Therefore, the gas pathway 13 and the flow-through device will not be blocked by the crystallization of the electrolyte.

Figure 5:
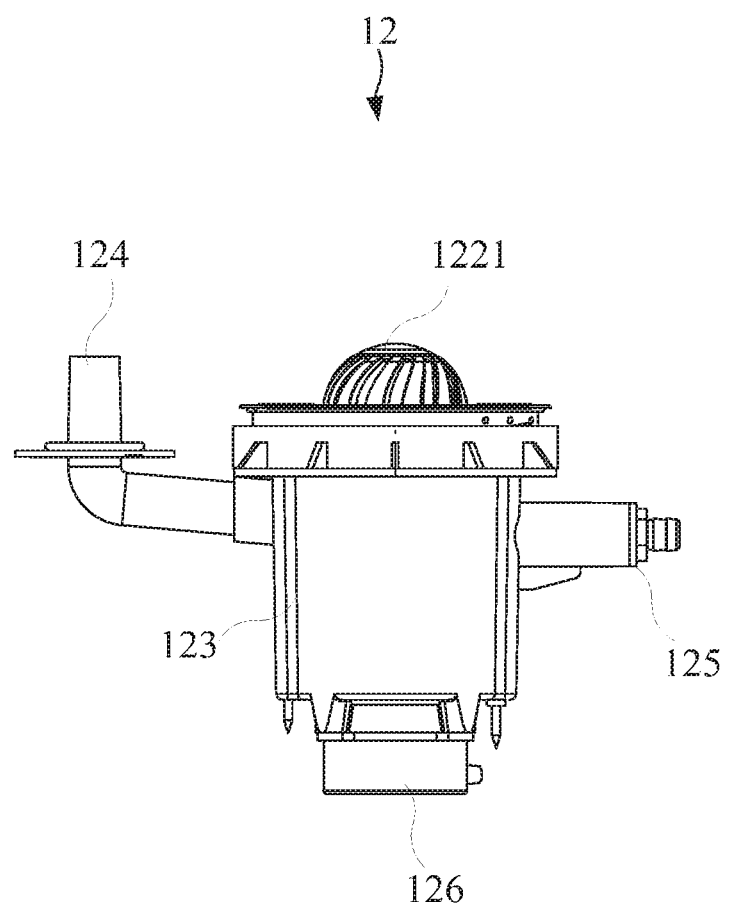
FIG. 5 illustrates a schematic diagram of atomizing device of the gas generator in an embodiment of the present invention.
Figure 6:
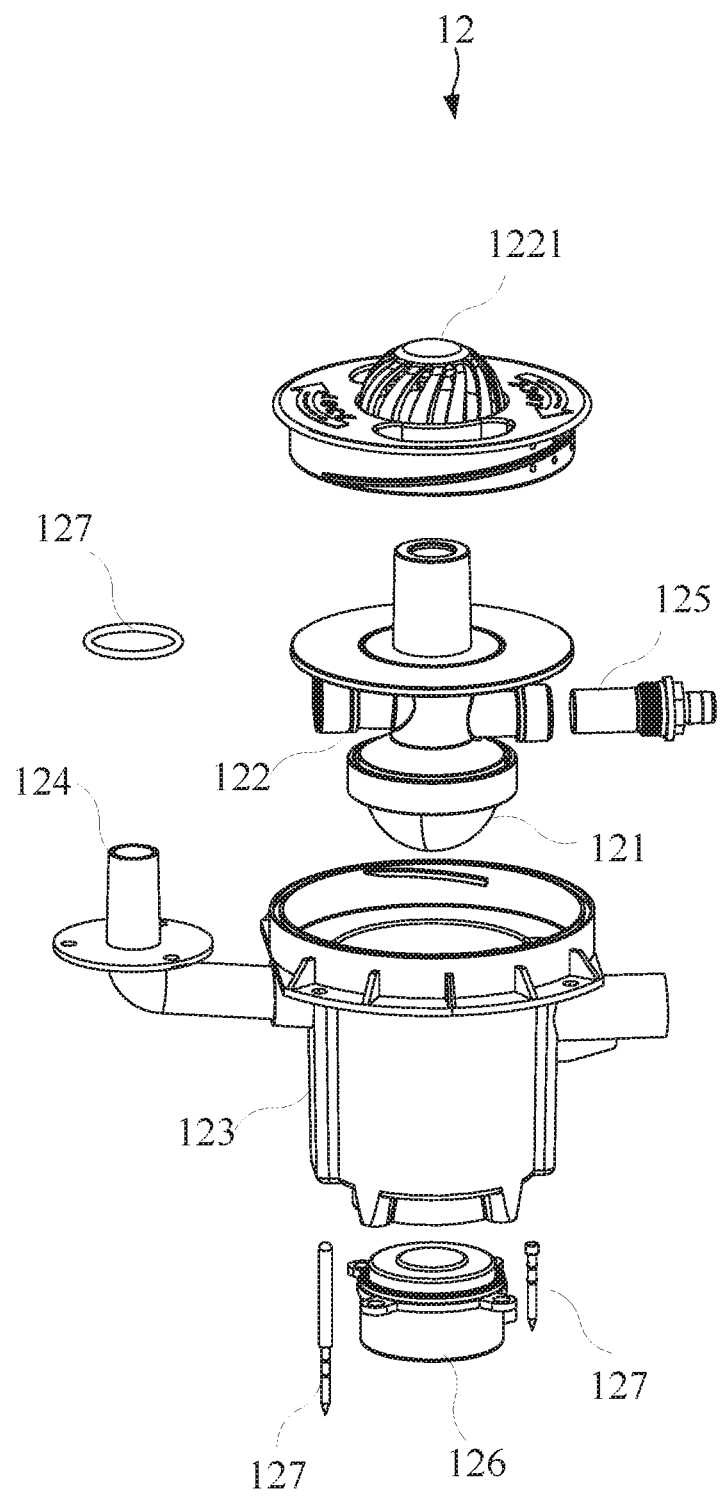
FIG. 6 illustrates an explosion diagram of atomizing device of the gas generator in an embodiment of the present invention.

Please refer to FIG. 5 and FIG. 6. FIG. 5 illustrates a schematic diagram of atomizing device 12 of the gas generator 1 in an embodiment of the present invention. FIG. 6 illustrates an explosion diagram of atomizing device 12 of the gas generator 1 in an embodiment of the present invention. The atomizing device 12 comprises an atomizing chamber 121 and a mixing reaction chamber 122. The atomizing chamber 121 is configured for generating the atomized gas, and the mixing reaction chamber 122 is coupled to the gas pathway 13 and the atomizing chamber 121, respectively, for receiving the gas with hydrogen to mix the atomized gas with the gas with hydrogen to generate the healthy gas. The atomized gas is selected from one of the groups consisting of water vapor, atomized solution, volatile essential oil and combinations thereof.

In practical application, the atomizing device 12 can further comprise a shaker 126. The atomizing chamber 121 carries the required atomized gas precursor, and the shaker 126 is configured for oscillating the atomized gas precursor in the atomizing chamber 121 into the atomized gas as-needed.

In practice, the atomizing device 12 can further comprise a gas communication tube 125 for coupling the mixing reaction chamber 122 and the gas pathway 13. In addition, the atomizing device 12 comprises a healthy gas outlet 124 for the user to breathe in the healthy gas.

Besides, the atomizing device 12 can further comprise an atomizing device shell 123 for fixing the position of the other parts of the atomizing device 12.

Further, the atomizing device 12 can comprise an anti-static element 127 provided at a position in contact with the gas with hydrogen or the healthy gas. The anti-static element 127 can be a conductor coupled to the atomizing device shell 123 by the anti-static element 127, and the anti-static element 127 is grounded through the atomizing device shell 123. Thus, the potential of the gas with hydrogen or the healthy gas and the environment make a potential balance, so that the charge will not accumulate to produce the static electricity or even the risk of gas explosion caused by the static electricity.

In practice, the mixing reaction chamber 122 additionally comprises an explosion-proof hole 1221 for preventing the gas with hydrogen from exploding in the gas pathway 13. The explosion-proof hole 1221 can be composed of a silicone. When an explosion of the gas with hydrogen or the healthy gas in the gas generator 1, the gas can be released through the most fragile explosion-proof hole 1221, thereby protecting the other devices within the gas generator 1 and the gas pathway 13 to avoid the possibility of causing damage to the device or even causing injury to the person.

In addition, the atomizing device 12 can comprise a gas flow valve for regulating the amount of exhausted of the healthy gas so that the user can adjust the intake amount.

In practice, when the electrolytic device 11 stops electrolyzing the electrolyzed water, the pump 16 generates negative pressure in the electrolytic device 11 to allow the electrolytic device 11 to supplement the replenished water to replenishing cup 15. Meanwhile, an impurity can be returned back to the electrolytic device 11 by the replenished water flowing through the gas pathway 13 to keep the gas pathway 13 clean. The impurity in the gas pathway 13 is electrolyte brought out by the gas with hydrogen. The solenoid valve can be activated to block the conduction between the first end 1412 and the second end 1413 of the first conduit 141, and make conduction between the third end 1421 of the second conduit and the first conduit 141. At the same time, the pump 16 can exhaust the gas in the electrolytic device 11 through the second conduit 142, so that the electrolytic device 11 generates negative pressure.

Please refer to FIG. 3 and FIG. 4 again. In an embodiment, the gas generator 1 can further comprise a collecting tank 17 provided on the outlet end of the three-way valve module 14 connected to the exterior of the gas generator 1, for condensing the gas with hydrogen and the volatile electrolyzed water contained in the electrolytic device 11 exhausted via the three-way valve module 14, wherein the collecting tank 17 can further comprise a plurality of condensate sheets to assist in condensing the gas with hydrogen and the volatile gases. Furthermore, since the second conduit 142 is a bi-directional pathway, the liquid water condensed by the collecting tank 17 can be returned to the electrolytic device 11 to reduce the loss of the electrolyzed water rich in electrolytes.

It is to be noted that the three-way valve module 14 described in the present embodiment is, but not limited to, coupled in a schematic manner as the schematic diagram of FIG. 7. That is, both ends of the first end 1412 and the third end 1422 are coupled to the electrolytic device 11 and the second end 1413 of the first conduit 141 is coupled to the collecting tank 17 or the external environment to conduct to the atmospheric pressure. For example, in the gas generator 1 of the present invention, the first end 1412 of the three-way valve module 14 is coupled to the electrolytic device 11, and the second end 1413 is connected to the exterior of the gas generator 1 to form a first conduit 141, and then the third end 1421 of the second conduit 142 is coupled to the switch, and the fourth end 1422 is coupled to the collecting tank 17, or other types of connections having the same effect.

In practice, when the gas generator 1 is turned off, the electrolytic device 11 stops electrolyzing the electrolyzed water to generate the gas with hydrogen and does not supplement the replenished water to the electrolytic device 11, and the solenoid valve is de-activated to prevent the electrolytic device 11 from be connected with the exterior of the gas generator 1 through the second conduit 142 and simultaneously makes the first conduit 141 so that the electrolytic device 11 is connected to the exterior of the gas generator 1. Although the electrolyzed water in the electrolytic device 11 can be controlled by the water level gauge when the gas generator 1 is operated, the heat is generated when the electrolytic device 11 is operated, and when the gas generator 1 is shutdown, negative pressure is generated in the electrolytic device 11 due to the decrease in temperature. If the electrolytic device 11 is not connected to the outside through the first conduit 141 or the second conduit 142, the electrolytic device 11 will draw in the outside moisture or liquid water in order to keep the pressure equal to the outside pressure, resulting in an electrolytic solution in the electrolytic device 11 higher than expected leading to the risk of leakage of electrolyte or corrosion of electronic components. The present invention can maintain the pressure of the electrolytic device 11 through the first conduit 141 so that the electrolytic device 11 does not raise the electrolyte due to excessive replenishment of the replenished water, and if the collecting tank 17 is connected to the atmospheric end of the first conduit 141 at this time, the liquid cooled by the sump 17 can be returned to the electrolytic device 11. Due to the function of the one-way valve 1411 of the first conduit 141, the electrolyzed water can be prevented from flowing out of the first conduit 141 when the electrolytic device 11 is toppled over or volatile.

To summarize, the objective of the present invention is to provide a gas generator comprising the electrolytic device, the gas pathway, the replenishing cup, and the three-way valve module. The gas with hydrogen generated by the electrolytic device in the gas generator of the present invention is for inhaling. The three-way valve module is provided in the electrolytic device, in order to adjust the pressure inside the electrolytic device, so that the liquid level of the electrolyzed water does not become unpredictable due to the pressure difference, thereby avoiding the electrolyzed water splashing or corroding the other elements.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
    an electrolytic device for accommodating electrolyzed water and for electrolyzing the electrolyzed water to generate gas with hydrogen;
    a gas pathway coupled to the electrolytic device for transferring the gas with hydrogen;
    a replenishing cup for accommodating a replenished water to supplement the replenished water to the electrolytic device; and
    a three-way valve module comprising a first conduit and a switch, wherein a first end of the first conduit is coupled to the electrolytic device and a second end of the first conduit is connected to the exterior of the gas generator, and the switch selectively couples the first end to the second end;
    wherein when the electrolytic device stops electrolyzing the electrolyzed water and the replenishing cup stops supplementing the replenished water to the electrolytic device, the switch couples the first end to the second end, such that the electrolytic device is connected to the exterior of the gas generator via the first conduit.

2. The gas generator of claim 1, wherein the three-way valve module comprises a one-way valve configured in the first conduit, and the one-way valve only allows the external gas of the gas generator to flow into the electrolytic device unidirectionally.

3. The gas generator of claim 1, wherein when the electrolytic device stops electrolyzing the electrolyzed water and the replenishing cup supplements the replenished water to the electrolytic device, the switch blocks the conduction between the first end and the second end.

4. The gas generator of claim 3, further comprising a pump coupled to the electrolytic device, wherein when the electrolytic device stops electrolyzing the electrolyzed water and the replenishing cup supplements the replenished water to the electrolytic device, the pump generates negative pressure within the electrolytic device.

5. The gas generator of claim 4, wherein the three-way valve further comprises a second conduit, and a third end of the second conduit is coupled to the switch and a fourth end of the second conduit is coupled to the electrolytic device or connected to the exterior of the gas generator, the pump is configured in the second conduit; when the electrolytic device stops electrolyzing the electrolyzed water and the replenishing cup supplements the replenished water to the electrolytic device, the switch couples the first conduit to the second conduit, so that the electrolytic device is connected to the exterior of the gas generator.

6. The gas generator of claim 5, wherein when the electrolytic device stops electrolyzing the electrolyzed water and the replenishing cup stops supplementing the replenished water to the electrolytic device, the switch blocks the conduction between the first conduit and the second conduit.

7. The gas generator of claim 5, wherein when the electrolytic device electrolyzes the electrolyzed water, the switch blocks the conduction between the first conduit and the second conduit.

8. The gas generator of claim 1, wherein the switch can be a solenoid valve; when the solenoid valve is activated, the solenoid valve blocks the conduction between the first end and the second end.

9. The gas generator of claim 1, wherein the gas generator further comprises an atomizing device coupled to the gas pathway for generating atomized gas and receiving the gas with hydrogen to mix the atomized gas with the gas with hydrogen to generate healthy gas.

10. The gas generator of claim 1, wherein the replenishing cup is coupled to the gas pathway.

11. A gas generator, comprising:
an electrolytic device for accommodating electrolyzed water and for electrolyzing the electrolyzed water to generate gas with hydrogen;
a condensation filter coupled to the electrolytic device for condensing and filtering the gas with hydrogen;
a gas pathway coupled to the electrolytic device for transferring the gas with hydrogen;
a replenishing module for accommodating a replenished water, the replenishing module being configured to supplement the replenished water to the electrolytic device;
a valve module comprising a first conduit, and a second conduit, the first conduit coupled to the electrolytic device, and the valve module selectively coupling the first conduit to the second conduit; and
a pump coupled to the valve module;
wherein when the electrolytic device electrolyzes the electrolyzed water, the valve module decouples the first conduit from the second conduit, and the gas with hydrogen is transported to the condensation filter and the replenishing module; when the electrolytic device stops electrolyzing the electrolyzed water and the replenishing module supplements the replenished water to the electrolytic device, the valve module couples the first conduit to the second conduit, and the water in the replenishing module is drawn by the pump to the electrolytic device through the condensation filter.

12. The gas generator of claim 11, wherein the condensation filter is vertically stacked above the electrolytic device.

13. The gas generator of claim 11, wherein a first end of the first conduit is coupled to the electrolytic device, and a second end of the first conduit is connected to the exterior of the gas generator; when the electrolytic device stops electrolyzing the electrolyzed water and the replenishing module supplements the replenished water to the electrolytic device, the valve module blocks the conduction between the first end and the second end.

14. The gas generator of claim 13, wherein when the electrolytic device stops electrolyzing the electrolyzed water and the replenishing module supplements the replenished water to the electrolytic device, the pump generates negative pressure within the electrolytic device.

15. The gas generator of claim 13, wherein when the electrolytic device stops electrolyzing the electrolyzed water and the replenishing module supplements the replenished water to the electrolytic device, the valve module couples the first conduit to the second conduit, and the electrolytic device is connected to the exterior of the gas generator via the second conduit.

16. The gas generator of claim 11, wherein when the electrolytic device stops electrolyzing the electrolyzed water and the replenishing module stops supplementing the replenished water to the electrolytic device, the valve module makes the electrolytic device connected to the exterior of the gas generator via the first conduit.

17. The gas generator of claim 16, wherein when the electrolytic device stops electrolyzing the electrolyzed water and the replenishing module stops supplementing the replenished water to the electrolytic device, the valve module blocks the conduction between the first conduit and the second conduit.

18. The gas generator of claim 11, wherein the gas generator further comprises an atomizing device vertically spaced apart from the electrolytic device.

19. The gas generator of claim 11, wherein the gas generator further comprises an atomizing device coupled to the gas pathway for generating atomized gas and receiving the gas with hydrogen to mix the atomized gas with the gas with hydrogen to generate healthy gas.

20. The gas generator of claim 11, wherein the gas generator further comprises an anti-static element disposed in a position in contact with the gas with hydrogen or the healthy gas and the anti-static element is a conductor.

* * * * *